(12) United States Patent
Wei et al.

(10) Patent No.: US 7,438,935 B2
(45) Date of Patent: Oct. 21, 2008

(54) PHARMACEUTICAL COMPOSITION FOR THE TREATMENT OF CARDIOVASCULAR AND CEREBROVASCULAR DISEASES

(75) Inventors: Feng Wei, Tianjin (CN); Dekun Li, Tianjin (CN); Chongnian Luo, Tianjin (CN); Hongshui Yue, Tianjin (CN); Qingchuang Chen, Tianjin (CN); Zhijuan Huang, Tianjin (CN)

(73) Assignee: Tianjin Tasly Pharmaceutical Co., Ltd. (CN)

( * ) Notice: Subject to any disclaimer, the term of this patent is extended or adjusted under 35 U.S.C. 154(b) by 0 days.

(21) Appl. No.: 10/572,083

(22) PCT Filed: Sep. 23, 2004

(86) PCT No.: PCT/CN2004/001085
§ 371 (c)(1), (2), (4) Date: Sep. 19, 2006

(87) PCT Pub. No.: WO2005/051404
PCT Pub. Date: Jun. 9, 2005

(65) Prior Publication Data
US 2007/0053999 A1    Mar. 8, 2007

(30) Foreign Application Priority Data
Sep. 23, 2003    (CN) ............................... 03 1 44311

(51) Int. Cl.
*A61K 36/25*    (2006.01)
*A61K 36/537*    (2006.01)
*A61K 36/00*    (2006.01)

(52) U.S. Cl. .................. 424/728; 424/746; 424/725; 424/773

(58) Field of Classification Search .................. None
See application file for complete search history.

(56) References Cited

FOREIGN PATENT DOCUMENTS

CN    1375316 A  * 10/2002

OTHER PUBLICATIONS

"Observation on Effectiveness of Treatment of Coronary Heart Disease by Using Radix Salviae Miltiorrhizae Injection Combined with Radix Astragali Injection in 58 Cases" Wang, Li et al., "Chinese Journal of Traditional Medical Science and Technology" vol. 9 (4), p. 252, 2002.

"The Treatment of Coronary Heart Disease and Angina by Using The Method of Warming Yang Resolving Blood Stasis", Cao, Luyu et al., "Journal of Tianjin Institute of Traditional Chinese Medicine" vol. 21 (2), p. 35, Jun. 2002.

* cited by examiner

*Primary Examiner*—Christopher R. Tate
(74) *Attorney, Agent, or Firm*—Harness, Dickey & Pierce, P.L.C.

(57) ABSTRACT

The present invention discloses a pharmaceutical composition for the treatment of cardiovascular and cerebrovascular diseases which comprises Radix Salviae Miltiorrhizae extract 5.0%-70.0%, Radix Notoginseng extract 10.0%-85.0%, Radix Astragali extract 5.0%-70.0%, and Bomeol or oil of Lignum Dalbergiae Odoriferae 1.0%-15.0%. The composition is active against cerebral ischemia and myocardial ischemia. The effects are superior to total phenic acid of Radix Salviae Miltiorrhizae or total saponin of Radix Notoginseng respectively, or the combination thereof. The composition of the invention can provide various kinds of preparations by the addition of various accessories. Thus the invention provides a more effective and convenient composition of TCM effective sections and its preparations.

14 Claims, 2 Drawing Sheets

PHARMACEUTICAL COMPOSITION FOR THE TREATMENT OF CARDIOVASCULAR AND CEREBROVASCULAR DISEASES

TECHNICAL FIELD

The invention relates to a medicament composition. In particular, it relates to a pharmaceutical composition for the treatment of cardiovascular and cerebrovascular diseases.

BACKGROUND ART

Statistics has shown that the morbidity and mortality of cardiovascular and cerebrovascular diseases in China have been increasing for the last five decades. During the 1950's to 1960's, cardiovascular and cerebrovascular diseases ranked fifth and sixth of all the diseases causing deaths. Since 1975, however, they have ascended to the second and third places respectively, and the death caused by cardiovascular and cerebrovascular diseases has been taking the first place in all deaths caused by diseases. As a matter of fact, the mortality of cardiovascular and cerebrovascular diseases in Chinese accounted for 42.6% of all the deaths in 2001 from 12.07% in 1975. Nowadays, they cause about 2 millions deaths every year. Some patients survive, but most of the survivors are disabled and unable to take care of themselves in their daily life, which causes heavy burdens for their families and the society.

Cardiovascular and cerebrovascular diseases are also the leading causes of deaths in western countries. Based on the current epidemiological data, it is estimated that till 2020, coronary artery disease and cerebral hemorrhage are still the first and second causes of death of human being, even though the order of the death causes due to human diseases will be changed significantly. It is estimated that up till then, the global deaths of coronary artery disease will increase from 6.3 millions in 1990 to 11 millions; and the deaths of cerebral hemorrhage will be up from 4.4 millions to 7.7 millions. During these 30 years, the death caused by circular system diseases will increase to 59.6%. The deaths of coronary artery disease and stroke will increase 74.6% and 75%, respectively. All these data show that cardiovascular and cerebrovascular diseases are not only the main diseases affecting harm human health; they are also the current and will remain the 'No. 1 killer' leading to death or disability.

Among the therapeutic drugs for treating cardiovascular and cerebrovascular diseases, traditional Chinese patent medicines and Western medicines are administered with effects focusing on different aspects; traditional Chinese patent medicines have less side effects, and therefore have taken a good share of the market. Among the available traditional Chinese patent medicines for the treatment of cardiovascular and cerebrovascular diseases, those comprising, as active components, active ingredients of biological effective parts of herbs, such as notoginsenoside, salvianolic acid, radix puerarine isoflavones, and gypenosides, are attracting more and more attentions. Since the biological effective parts in the traditional Chinese patent medicine herbs for treating cardiovascular and cerebrovascular diseases have achieved respective functions and effects focusing on different aspects, they are expected to find potential wide use in combined administration. On the other hand, currently, the traditional Chinese patent medicines based on single biological effective part of herbs, especially in the form of injection solutions, such as XUESAITONG, XUESHUANTONG (trade names), fall short of the demand for combined administration. Furthermore, simply mixing some traditional Chinese patent medicines injection solutions without the previous approval of State Food and Drug Administration represents a great risk of unexpected adverse reactions, such as rapid blood pressure increase, fever, and allergy. Therefore, it will be very important to provide more effective and convenient compositions of biologically active parts of herbs for clinical applications.

SUMMARY OF THE INVENTION

Accordingly, it is an object of the present invention to provide a more effective and convenient composition of bioactive parts of herbs and a preparation thereof for the treatment of cardiovascular and cerebrovascular diseases, which makes it possible to overcome the defects of the traditional Chinese patent medicines based on single biologically active parts of herbs which cannot satisfy the clinical need for combined administration, and avoid potential side reactions associated with simply mixing drugs together.

The present invention can be implemented as outlined in the following embodiments.

The pharmaceutical compositions of the present invention comprising
 Radix Salviae Miltiorrhizae extract;
 Radix Notoginseng extract;
 Radix Astragali extract; and
 Borneol or oil of Lignum Dalbergiae Odoriferae.

In an preferred embodiment of the present invention, the inventive composition comprising
 5.0%-70.0% Radix Salviae Miltiorrhizae extract;
 10.0%-85.0% Radix Notoginseng extract;
 5.0%-70.0% Radix Astragali extract; and
 1.0%-15.0% Borneol or oil of Lignum Dalbergiae Odoriferae.

In a further preferred embodiment of the present invention, the inventive composition comprising
 15.0%-50.0% Radix Salviae Miltiorrhizae extract;
 25.0%-65.0% Radix Notoginseng extract;
 15.0%-50.0% Radix Astragali extract; and
 2.0%-12.0% Borneol or oil of Lignum Dalbergiae Odoriferae.

In a still further preferred embodiment of the present invention, the inventive composition comprising
 20.0%-30.0% Radix Salviae Miltiorrhizae extract;
 30.0%-55.0% Radix Notoginseng extract;
 20.0%-30.0% Radix Astragali extract; and
 4.0%-10.0% Borneol or oil of Lignum Dalbergiae Odoriferae.

In a still further preferred embodiment of the present invention, the inventive composition comprising
 23% Radix Salviae Miltiorrhizae extract;
 45.0% Radix Notoginseng extract;
 23% Radix Astragali extract; and
 9% Borneol or oil of Lignum Dalbergiae Odoriferae.

In a still further preferred embodiment of the inventive composition, said Radix Salviae Miltiorrhizae extract comprises 45%-70% salvianolic acid B, 2%-10% salvianolic acid E, 4%-20% rosmarinic acid, 1%-10% lithospermic acid, and more than 70% salvinolic acids.

In a still further preferred embodiment of the inventive composition, said Radix Notoginseng extract comprises 2%-10% notoginsenoside R1, 2%-6% ginsenoside Re, 15%-40% ginsenoside Rg1, 15%-40% ginsenoside Rb1, 5%-12% ginsenoside Rd, and more than 70%, prefereably more than 80%, radix notoginseng saponins.

In a still further preferred embodiment of the inventive composition, said Radix Astragali extract comprises 5%-15% astragaloside I and more than 70% Radix Astragali saponins.

In a still further preferred embodiment of the inventive composition, said Radix Salviae Miltiorrhizae extract comprises more than 80% salvinolic acids; said Radix Notoginseng extract comprises more than 80% radix notoginseng saponins; and said radix astragali extract comprises more than 80% radix astragali saponins.

In a still further preferred embodiment of the inventive composition, it is injection, tablets, sustained-release tablets, drop pills, granules, injection powder, capsules, and microgranule.

In a still further preferred embodiment of the inventive composition, it is an injection or injection powder.

The inventive composition is used for the treatment of cardiovascular and cerebrovascular diseases.

The Radix Salviae Miltiorrhizae extract of the above pharmaceutical compositions can be prepared by the means of the prior art processes, for example, by the process disclosed in patent applications CN1352985A, CN1247855A, CN1242364A, CN1384090A, CN1459448A, and Guo Ying et al., *The Journal of Yunnan University of Traditional Chinese Medicine,* 2001, 24(4): 6. It can also be obtained by the processes similar to the above with appropriate modifications.

The present Radix Salviae Miltiorrhizae extract comprises 45%-70% salvianolic acid B, 2%-10% salvianolic acid E, 4%-20% rosmarinic acid, 1%-10% lithospermic acid, and more than 70%, preferably more than 80%, salvinolic acids. Irrespective of preparation process of the Radix Salviae Miltiorrhizae extract, the expression "Radix Salviae Miltiorrhizae extract" as used herein means that the content of the extracts falls within the scopes as listed; and for that purpose, the crude extracts can be further refined, such as by concentration, to meet the requirements in terms of the content of the components. The components and their content can be characterized and determined as follows respectively:

1. Determination of the Contents of Salvianolic Acid B, Salvianolic Acid E, Rosmarinic Acid, and Lithospermic Acid in Radix Salviae Miltiorrhizae Extract (HPLC)

a. Chromatographic Conditions
   Filler: Octadecylsilyl-Silica Gel.; Mobile phase:acetonitrile-water-phosphoric acid (23.5:76.5:0.02); Detection wavelength: 288 nm.
   Theoretic plates is not lower than 5000, calculated based on the peak of salvianolic acid B.

b. Preparation of Control Solutions:
   0.2 mg/ml Salvianolic acid B control solution is prepared by mixing the control sample with the mobile phase. likewise, also prepared are 0.02 mg/ml Salvianolic acid E control solution, 0.05 mg/ml Rosmarinic acid control solution, and 0.01 mg/ml Lithospermic acid control solution.

c. Preparation of Sample Solutions:
   35 mg of Radix Salviae Miltiorrhizae extract is weighted accurately into a 25 ml measuring bottle. To the bottle is added the mobile phase to dissolve the sample. The resultant solution is further diluted with simultaneous shaking to 25 ml with mobile phase. 5 ml sample solution is taken into a 25 ml measuring bottle, and to the bottle is added the mobile phase to make up to 25 ml, shake the resultant solution to make it thoroughly mixed.

d. The Assay Procedure
   10 μl of each control solutions and sample solutions are assayed on the liquid chromatograph respectively.

2. Determination of Salvinolic Acids in the Above Radix Salviae Miltiorrhizae Extract (Spectrophotometry)

a. Preparation of Control Solutions:
   20 μg/ml Salvianolic acid B solution is prepared by mixing the sample with the mixture of acetonitrile-water-phosphoric acid (23.5:76.5:0.02).

b. Preparation of Sample Solutions:
   25 mg of Radix Salviae Miltiorrhizae extract is weighted accurately into a 50 ml measuring bottle. To the bottled is added the mixture of acetonitrile-water-phosphoric acid (23.5:76.5:0.02). The resultant solution is diluted with simultaneous shaking to 25 ml with the said mixture. 2 ml sample solution is taken accurately into a 50 ml measuring bottle. The said mixture is added and made up to 25 ml, shake the resultant solution to make it thoroughly mixed.

c. The Assay Procedure
   Take acetonitrile-water-phosphoric acid (23.5:76.5:0.02) as blank, the absorption value of the control solutions and sample solutions is determined individually under the wavelength of 288 nm using Spectrophotometry (*China Pharmacopoeia,* edition 1995, volume 1, appendix VA). The calculations are based on the following formula:

$$\text{Salvinolic acids } (\%) = f(A-B) + B$$

Wherein, f is 0.626, correction factor; A is the content of salvinolic acids determined by spectrophotometry against salvianolic acid B; B is the content of salvianolic acid B determined by HPLC.

3. HPLC Fingerprint Spectrum of Said Radix Salviae Miltiorrhizae Extract

For the determination method, reference is made to the description in connection with the determination of salvianolic acid B and E, rosmarinic acid, lithospermic acid in the above (1). The recording duration of time is 60 minutes.

Of all common fingerprint peaks, the peak of salvianolic acid B, a common peak representing a relatively big and stable peak area, is selected as the reference peak. The relative retention time and relative peak area are calculated against the retention time and peak area of the reference peak. There are 5-7 common peaks in the fingerprint of the above Radix Salviae Miltiorrhizae extract, and there are typically 6 common peaks. The relative retention times of the 6 common peaks are in order 0.55-0.65 (peak of salvianolic acid E), 0.66-0.70 (peak of rosmarinic acid), 0.71-0.79 (peak of lithospermic acid), 1 (peak of salvianolic acid B), 1.03-1.12, 1.21-1.30. Of all the common peaks, only the peak of salvianolic acid B, the reference peak, has a ratio of single peak area to total peak area greater than 20%. The peak area of salvianolic acid B accounts for 57%-87% of total peak area; its relative peak area is 1. With relative retention time of 0.66-0.70, the peak area of the common peak of rosmarinic acid accounts for 3%-18% of total peak area; and its relative peak area is 0.03-0.25. The total peak area of non-common peak is less than 10% of total peak area.

The Radix Notoginseng extract of the above pharmaceutical compositions can be prepared by the means of the prior art processes, for example, by the process disclosed in Chinese patent ZL1095363C, Chinese patent application CN1352985A, Qian Tianxiang et al., *Foreign Medical Sciences, Plant Medicine Section,* 1997, 12(4)), Tang Diguang, *The journal of Chinese Traditional Patent Medicine,* 1990, 12(8): 5, *The Standard of Public Health Ministry of China* WS3-B-3590-2001 (z). It can also be obtained by the processes similar to the above with appropriate modifications. It is also commercially available in the market, such as in the form of an extract comprising 95% (determined by UV) Radix Notoginseng Saponins (Rb1≧30%, Rg1≧20%, R1≧15%, determined by HPLC).

The present Radix Notoginseng extract comprises 2%-10% notoginsenoside R1, 2%-6% ginsenoside Re, 15%-40% ginsenoside Rg1, 15%-40% ginsenoside Rb1, 5%-12% ginsenoside Rd, and more than 70%, prefereably more than 80%, radix notoginseng saponins. Irrespective of preparation process of the Radix Notoginseng extract, the expression "Radix Notoginseng extract" as used herein means that the contents of the extracts fall within the scopes as listed; and for that purpose, the crude extracts can be further refined, such as by concentration, to meet the requirements in terms of the contents of the components. The components and their content can be characterized and determined as follows respectively:

1. Determination of the Contents of Ginsenoside Re, Ginsenoside Rd, Notoginsenoside R1, Ginsenoside Rg1, and Ginsenoside Rb1 in Radix Notoginseng Extract (HPLC)

a. Chromatographic Conditions and System Suitability Test

Filler: Octadecylsilyl-Silica Gel; Column Temp: 40° C.; Flow Rate: 0.7 ml/min; Detection wavelength: 203 nm; Gradient of Mobile Phase as follows:

| Time | Water | Acetonitrile |
   | --- | --- | --- |
   | 0 | 70 | 30 |
   | 10 | 70 | 30 |
   | 30 | 10 | 90 | b. Preparation of Control Solutions:

0.2 mg/ml ginsenoside Re control solution is prepared by mixing the control sample with methanol. likewise, also prepared are 0.4 mg/ml ginsenoside Rd control solution, 0.2 mg/ml ginsenoside R1 control solution, 0.4 mg/ml notoginsenoside Rg1 solution and 0.4/ml ginsenoside Rb1 control solution respectively.

c. Preparation of Sample Solutions:

20 mg of the Radix Notoginseng extract is weighted accurately into a 50 ml measuring bottle. To the bottle is added the mobile phase to dissolved the sample. The resultant solution is further diluted with simultaneous shaking to 50 ml with the mobile phase.

d. The Assay Procedure

10 µl of each standard solutions and sample solutions is injected into the HPLC system, and is analyzed. The HPLC spectrum of Radix Notoginseng extract of present invention is then obtained.

(1) Determination of Radix Notoginseng Saponins in the above radix notoginseng extract (Spectrophotometry)

(2) HPLC Fingerprint Spectrum of the Radix Notoginseng extract

The determination method is referring to the description of ginsenoside Re, ginsenoside Rd, ginsenoside R1, notoginsenoside Rg1 and ginsenoside Rb1 above (1) by HPLC. The recording duration of time is 30 minutes.

Of all common fingerprint peaks, the peak of ginsenoside Rg1, representing a relatively big and steady peak area, is selected as reference peak. The relative retention time and relative peak area are calculated against the retention time and peak area of reference peak. There are 9-12 common peaks in the fingerprint spectrum of the above Radix Notoginseng extract, and there are typically 11 common peaks. The relative retention times of the 11 common peaks are in order 0.77-0.85 (peak of notoginsenoside R1), 0.87-0.97 (peak of ginsenosie Re), 1 (peak of ginsenoside Rg1, ie. reference peak), 2.58-2.67, 0.68-2.76, 2.77-2.81, 2.82-2.91 (peak of ginsenoside Rb1), 2.95-3.03, 3.05-3.13, 3.15-3.22 (peak of ginsenoside Rd), 3.24-3.91. Of all the common peaks, only the peak of ginsenoside Rg1 and the peak of ginsenosde Rb1 have the ratio of single peak area to total peak area greater than 20%. The peak area of ginsenoside Rg1, the reference peak, accounts for 20%-35% of total peak area; its relative peak area is 1. The peak area of ginsenoside Rb1 accounts for 30%-50% of total peak area; its relative peak area is 0.85-2.50. The peak area of notoginsenoside R1 accounts for 2%-8% of total peak area; its relative peak area is 0.06-0.40. The peak area of ginsenoside Rd accounts for 5%-14% of total peak area; its relative peak area is 0.14-0.70. The total peak area of non-common peak is less than 10% of total peak area.

The Radix Astragali extract of the above pharmaceutical composition can be prepared by the means of the prior art, for example, by the disclosures in China patent CN1096269C, Yu Hao et al., *West China Journal of Pharmaceutical Sciences*, 1993, 8(3):163, Teng Xinglong et al., *Heilongjiang Medical Journal*, 2002, 15(5): 340, Wang Zhijie et al., *Journal of Zhejiang College of Traditional Chinese Medicine*, 2001, 25(5): 43. It can also be obtained by the processes similar to the above with appropriate modifications. It is also commercially available in the market, such as in the form of an extract comprising 80%-98% (determinated by UV) Radix Astragali extract.

The present Radix Astragali extract comprises 5%-15% Astragaloside I and radix astragali saponins greater than 70%, or radix astragali saponins greater than 80% preferably. Irrespective of preparation process of the Radix Astragali extract, the expression "Radix Astragali extract" as used herein means that the contents of the extracts fall within the scopes as listed; and for that purpose, the crude extracts can be further refined, to meet the requirements in terms of the contents of the components.

The Borneol used in the above composition can be a naturally occurring or a synthesized one.

The oil of Lignum Dalbergiae Odoriferae used in the said composition can be obtained by distilling Lignum Dalbergiae Odoriferae.

The compositions of the present invention may be formulated into various dosage forms by combining with one or more pharmaceutically acceptable adjuvant. The said adjuvant include, but not limited to, starch, dextrin, lactose, microcrystalline cellulose (avicel), hydrooxypropyl methyl cellulose (HPMC), polyethylene glycol, magnesium stearate, micro silicon gel, xylitol, lactitol, glucose, glycine, D-mannitol and the like. The present pharmaceutical composition may take the forms of injections, tablets, sustained-release tablets, drop pills, granules, injection powder, capsules, microgranules and the like. Tablets, drop pills, injection powder, and capsules are preferred. The total content of salvinolic acids, radix notoginseng spaonins and radix astragali saponins are preferably over 80%, if the compositions of the present invention are formulated into injections or injection powder.

The raw materials of the inventive composition are easy to obtain and thus facilitate commercial production of the inventive composition. The present composition may be formulated into various forms as desired, and provide more convenient, efficient and high quality controlled modern Chinese traditional patent medicine for clinical applications.

The present invention compares the effects on anti-cerebral ischemia of the inventive compositions; salvinolic acids plus radix notoginseng saponins plus broneol or oil of lignum dalbergiae odoriferae; salvinolic acids plus radix notoginseng saponins; salvinolic acids and radix notoginseng saponins, using the model of the localized cerebral ischemia caused by applying iron (III) chloride hexahydrate locally on middle cerebral artery, and by the determination of the neurological symptoms and the area of cerebral infarction. The results show that the present composition has significant effect on anti-cerebral ischemia. Its therapeutic effects is more significant than that of single salvinolic acids or radix notoginseng saponins, more significant than that salvinolic acids plus radix notoginseng saponins, and more significant than salvinolic acids plus radix notoginseng saponins plus Broneol or oil of Lignum Dalbergiae Odoriferae. The results indicate that the pharmaceutical composition of present invention, i.e., the combination of Radix Salviae Miltiorrhizae extract plus Radix Notoginseng extract plus Radix Astragali extract and Broneol, or Radix Salviae Miltiorrhizae extract plus Radix Notoginseng extract plus Radix Astragali extract and oil of Lignum Dalbergiae Odoriferae, have significant synergic effect.

In the descriptions of present invention, all percentages are by weight, unless otherwise indicated.

DETAILED DESCRIPTION OF THE EMBODIMENTS

The invention will be better understood by reference to the examples that follow. The following examples are for illustrative purpose and are not intended to limit the scope of the invention.

EXAMPLE 1

Radix Salviae Miltiorrhizae Extract:

The Radix salviae miltiorrhizae extract was prepared by the method disclosed in Chinese patent application CN1459448A. Thus, 5 kg of Radix salviae miltiorrhizae was grounded into coarse powder and then extracted 3 times with deionized water at 100° C. under a mild boiling condition. For the first extraction, 27.5 kg water was added and heated for 1 hour; for the second and third extractions, 15 kg water was added and heated for 0.5 hour respectively. The acidity of the extract was adjusted to pH 2 with 10% HCl and then filtered. The filtrate was loaded onto a polyamide resin column (the amount of dry resin is two-thirds amount of the crude extract). The column was eluted with deionized water 5 times volume of the column, followed by 5 times column volume of 0.1% $NaHCO_3$ solution. The eluate was collected. After adjusting the pH to 2 with 10% HCl, the eluate was loaded onto $D_{101}$ macroporous absorptive resin. The resin was eluted with deionized water until the eluate became neutral. Then the column was eluted with 95% ethanol and the color band was collected. The collected solution was concentrated under reduced pressure until drying up. The dry material was dissolved in water and then stored in refrigerator over night. After filtering through 0.3 μm mixed cellulose micropore filter film, the salvinolic acids extract was obtained. It was adjusted to pH 6.0 with 2% NaOH solution and immediately lyophilized to yield 221 g frozen dry powder of Radix salviae miltiorrhizae extract material. The yield was 4.4% of crude material Radix salviae miltiorrhizae.

Figure 1:
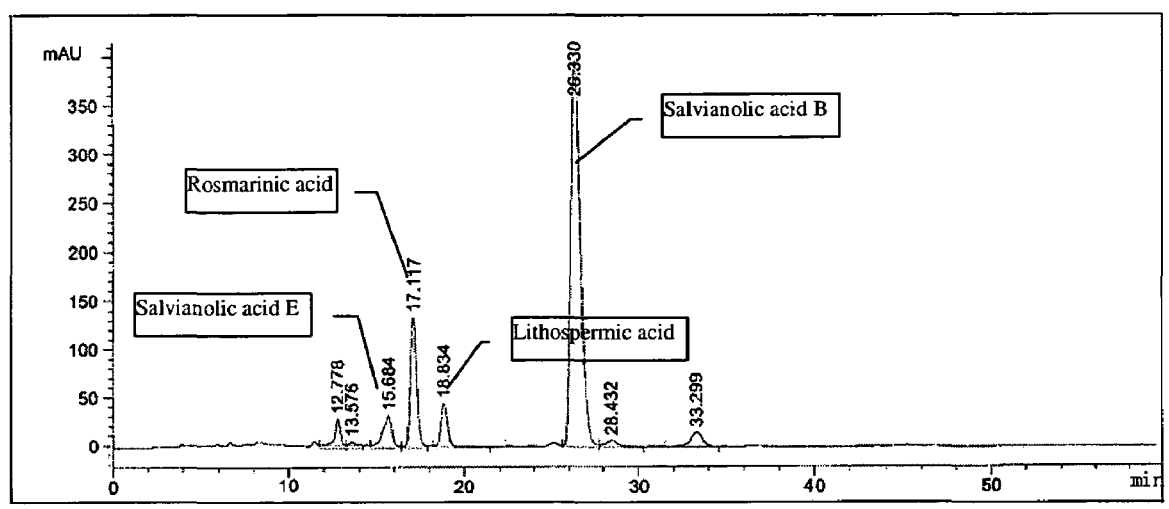
FIG. 1: HPLC fingerprint spectrum of Radix Salviae Miltiorrhiaze extract (0-60 min)

The Radix salviae miltiorrhizae extract so obtained contained salvianolic acid A, salvianolic acid B, salvianolic acid C, salvianolic acid D, salvianolic acid E, salvianolic acid G, miltionone I, rosmarinic acid, lithospermic acid, danshensu and so on. Wherein said salvianolic acid B was 53.73%, salvianolic acid E was 3.7%, rosmarinic acid was 5.2%, lithospermic acid is 1.7%, and salvinolic acids was 83.94%. There were 6 common peaks shown in HPLC fingerprint spectrum of the Radix salviae miltiorrhizae extract (the average of 10 batches). The averages of relative retention times for these 6 common peaks were, in the given order, 0.60 (peak of salvianolic acid E), 0.68 (peak of rosmarinic acid), 0.73 (peak of lithospermic acid), 1 (peak of salvianolic acid B), 1.08, 1.26. Of common peaks, only the peak of salvianolic acid B, which was reference peak, had the ratio of single peak area to total peak area greater than 20%. The peak area of salvianolic acid B accounted for 72% (average) of total peak area; and its relative peak area was 1; The peak area of rosmarinic acid accounted for 10% (average) of total peak area; and its relative peak area was 0.14 (average). The total peak area of non-common peaks was less than 10% of total peak area. The HPLC fingerprint spectrum of the Radix Salviae Miltiorrhizae is shown in FIG. 1.

Figure 2:
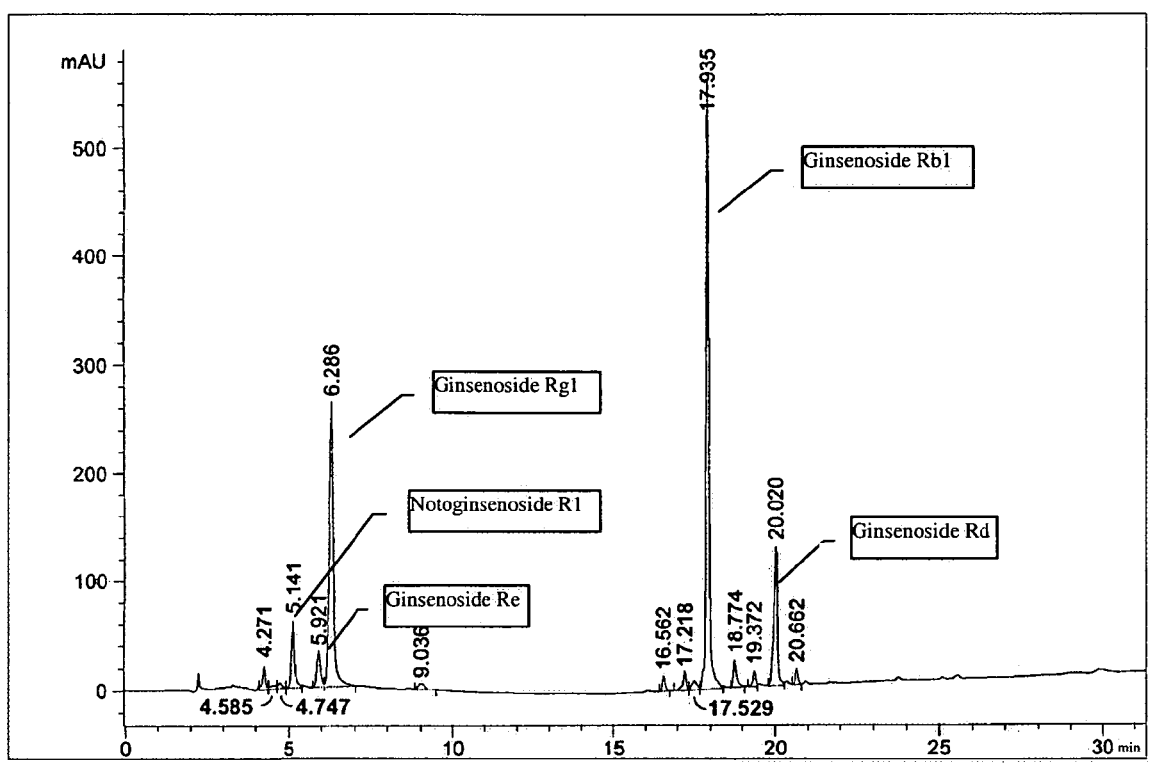
FIG. 2: HPLC fingerprint spectrum of Radix Notoginseng extract (0-30 min).

Radix Notoginseng Extract:

The radix notoginseng saponins that was commercial available was further refined to produce desired Radix Notoginseng extract. The extract obtained contained ginsenoside Rb1, ginsenoside Rd, ginsenoside Re, ginsenoside Rg1, ginsenoside Rg2, ginsenoside Rg3, ginsenoside Rh1, ginsenoside Rh2, panaxytriol, notoginsenoside R1, notoginsenoside R2, notoginsenoside R3, 20-gluco-ginsenoside Rf. Wherein, ginsenoside Re is 3.9%, ginsenoside Rg1 is 34.3%, ginsenoside Rb1 was 31.0%, ginsenoside Rd is 8.8%, notoginsenoside R1 was 6.8%, and radix notoginseng saponins was 94%. There were 11 common peaks shown in HPLC fingerprint spectrum (the average of 10 batches) of Radix notoginseng extract. The averages of relative retention times for these 11 common peaks were, in the given order, 0.82 (peak of notoginsenoside R1), 0.94 (peak of ginsenoside Re), 1 (peak of ginsenoside Rg1, reference peak), 2.63, 2.74, 2.79, 2.85 (peak of ginsenoside Rb1), 2.99, 3.08, 3.18 (peak of ginsenoside Rd), and 3.28. Of all common peaks, the peak of ginsenoside Rg1 and the peak of ginsenoside Rb1 had the ratio of single peak area to total peak area greater than 20%. The peak area of ginsenoside Rg1 (ie. reference peak) accounted for 28% (average) of total peak area; and its relative peak area was 1. The peak area of ginsenoside Rb1 accounted for 39% (average) of total peak area; and its relative peak area was 1.36 (average). The peak area of notoginsenoside R1 accounted for 6% (average) of total peak area; and its relative peak area was 0.20 (average). The peak area of ginsenoside Rd accounted for 10% (average) of total peak area; and its relative peak area was 0.37 (average). The total peak area of non-common peaks was less than 10% of total peak area. The HPLC fingerprint spectrum of the radix notoginseng is shown in FIG. 2.

Radix Astragali Extract:

The Radix Astragali extract that was commercial available was further refined. The extract obtained contained acetylastragaloside, astragaloside I, astragaloside II, astragaloside III, astragaloside IV, isoastragaloside I, isoastragaloside II, astramembrannin II, cycloastragenol, soyasaponin I, lupeod, β-sitosterol, daucosterin. Wherein, astragaloside I was 9.5% and the contents of the Radix Astragali extract was 88.9%.

75 mg of Radix Salviae Miltrorrhizae extract, 150 mg of Radix Notoginseng extract, 75 mg of Radix Astragali extract, all obtained from above and 30 mg Borneol were mixed sufficiently. Then the mixture was lyophilized to obtain the composition of the invention.

EXAMPLE 2

100 mg of Radix Salviae Miltrorrhizae extract, 200 mg of Radix Notoginseng extract, 75 mg of Radix Astragali extract, obtained from present example 1, and 30 mg oil of Lignum Dalbergiae Odoriferae were mixed with 400 mg polyethylene glycol-6000, and melted to give a mixture. Then the mixture was allowed to cool and the composition of the invention was obtained.

EXAMPLE 3

96 mg of Radix Salviae Miltrorrhizae extract, 136 mg of Radix Notoginseng extract, 70 mg of Radix Astragali extract, obtained from present example 1 and 28 mg Borneol were mixed sufficiently. Then the mixture was allowed to be lyophilized and the composition of the invention was obtained.

EXAMPLE 4

70 mg of Radix Salviae Miltrorrhizae extract, 150 mg of Radix Notoginseng extract, 90 mg of Radix Astragali extract, obtained from present example 1, and 20 mg of Borneol were mixed sufficiently. Then the mixture was allowed to be lyophilized to obtain the composition of the invention.

EXAMPLE 5

165 mg of Radix Salviae Miltrorrhizae extract, 80 mg of Radix Notoginseng extract, 60 mg of Radix Astragali extract, obtained from present example 1, and 25 mg of Borneol were mixed sufficiently. Then the mixture was allowed to be lyophilized to obtain the composition of the invention.

EXAMPLE 6

75 mg of Radix Salviae Miltrorrhizae extract, 135 mg of Radix Notoginseng extract, 82 mg of Radix Astragali extract, obtained from present example 1, and 38 mg of Borneol were mixed sufficiently. Then the mixture was allowed to be lyophilized to obtain the composition of the invention.

EXAMPLE 7

230 mg of Radix Salviae Miltrorrhizae extract, 75 mg of Radix Notoginseng extract, 17 mg of Radix Astragali extract, obtained from present example 1, and 8 mg of Borneol were mixed sufficiently. Then the mixture was allowed to be lyophilized to obtain the composition of the invention.

EXAMPLE 8

17 mg of Radix Salviae Miltrorrhizae extract, 70 mg of Radix Notoginseng extract, 230 mg of Radix Astragali extract, obtained from present example 1, and 13 mg of Borneol were mixed sufficiently. Then the mixture was allowed to be lyophilized to obtain the composition of the invention.

EXAMPLE 9

55 mg of Radix Salviae Miltrorrhizae extract, 160 mg of Radix Notoginseng extract, 63 mg of Radix Astragali extract, obtained from present example 1, and 48 mg of Borneol were mixed sufficiently. Then the mixture was allowed to be lyophilized to obtain the composition of the invention.

EXAMPLE 10

96 mg of Radix Salviae Miltrorrhizae extract, 136 mg of Radix Notoginseng extract, 70 mg of Radix Astragali extract, obtained from present example 1, and 28 mg oil of Lignum Dalbergiae Odoriferae were mixed sufficiently with 400 mg polyethylene glycol-6000, and fused. Then the mixture was allowed to cool and the composition of the invention was obtained.

EXAMPLE 11

70 mg of Radix Salviae Miltrorrhizae extract, 150 mg of Radix Notoginseng extract, 90 mg of Radix Astragali extract, obtained from present example 1, and 20 mg oil of Lignum dalbergiae odoriferae were mixed sufficiently with 400 mg polyethylene glycol-6000, and fused. Then the mixture was allowed to cool and the composition of the invention was obtained.

EXAMPLE 12

165 mg of Radix Salviae Miltrorrhizae extract, 80 mg of Radix Notoginseng extract, 60 mg of Radix Astragali extract, obtained from present example 1, and 25 mg oil of Lignum Dalbergiae Odoriferae were mixed sufficiently with 400 mg polyethylene glycol-6000, and fused. Then the mixture was allowed to cool and the composition of the invention was obtained.

EXAMPLE 13

75 mg of Radix Salviae Miltrorrhizae extract, 135 mg of Radix Notoginseng extract, 82 mg of Radix Astragali extract, obtained from present example 1, and 38 mg oil of Lignum Dalbergiae Odoriferae were mixed sufficiently with 400 mg polyethylene glycol-6000, and fused. Then the mixture was allowed to cool and the composition of the invention was obtained.

EXAMPLE 14

230 mg of Radix Salviae Miltrorrhizae extract, 75 mg of Radix Notoginseng extract, 17 mg of Radix Astragali extract, obtained from present example 1, and 8 mg oil of Lignum Dalbergiae Odoriferae were mixed sufficiently with 400 mg polyethylene glycol-6000, and fused. Then the mixture was allowed to cool and the composition of the invention was obtained.

EXAMPLE 15

17 mg of Radix salviae Miltrorrhizae extract, 70 mg of Radix Notoginseng extract, 230 mg of Radix Astragali extract, obtained from present example 1, and 13 mg oil of Lignum Dalbergiae Odoriferae were mixed sufficiently with 400 mg polyethylene glycol-6000, and fused. Then the mixture was allowed to cool and the composition of the invention was obtained.

EXAMPLE 16

55 mg of Radix Salviae Miltrorrhizae extract, 160 mg of Radix Notoginseng extract, 63 mg of Radix Astragali extract, obtained from present example 1, and 48 mg oil of Lignum Dalbergiae Odoriferae were mixed sufficiently with 400 mg polyethylene glycol-6000, and fused. Then the mixture was allowed to cool and the composition of the invention was obtained.

EXAMPLE 17

75 g of Radix Salviae Miltrorrhizae extract, 135 g of Radix Notoginseng extract, 96 g of Radix Astragali extract, obtained from present example 1, and 25 g of Borneol, 90 g mannitol, 15 g calcium disodium edate, and 15 ml distilled water were mixed sufficiently. Then the mixture was allowed to be lyophilized and divided into 1000 aliquots.

EXAMPLE 18

67 g of Radix Salviae Miltrorrhizae extract (CN Pat. Application CN1352985A, example 1), 180 g of Radix Notoginseng extract (example 1 of the invention), 67 g of Radix Astragali extract (example 1 of the invention), and 16 g Borneol were mixed sufficiently with 40 g microcrystalline cellulose. 3% povidone-ethanol solution was added to soften the mixture. The mixture was then passed through 18# sieve to form granules and dried at 60° C. for 30-45 minutes. So obtained granules were then trimed, and 4 g talc was added and mixed thoroughly. The formed granules were filled into capsule.

EXAMPLE 19

50 g of Radix Salviae Miltrorrhizae extract (prepared according to water extraction and alcohol precipitation method, Guo Ying et al, *The Journal of Yunnan University of Traditional Chinese Medicine,* 2001, 24(4): 6), 210 g of the Radix Notoginseng extract (Qian Tian Xiang et al. *Foreign Medical Sciences, Plant Medicine Section,* 1997, 12(4)), 50 g of Radix Astragali extract (example 1 of the invention), and 20 g Borneol were dissolved individually with a small amount of physiological saline. Appropriate amount of Tween 80 was then added. Each mixture was finely grinded, and decolorized after physiological saline was added. The solution was filtered under reduced pressure until it became clear and transparent. The filtrate was collected into a container containing physiological saline. The container was sealed and sterilized by boiling water. The three kinds of clear solutions were then mixed and the acidity was adjusted to 5. Appropriate volume of physiological saline was added. The filtering process was repeated to get clear and transparent solution. The desired injection was obtained.

EXAMPLE 20

60 g of Radix Salviae Miltrorrhizae extract (CN Pat. Application CN1384090A, example 1), 80 g of Radix Notoginseng extract (Tang Di Guang, *The journal of Chinese Traditional Patent Medicine,* 1990, 12(8): 5), 165 g of Radix Astragali extract (example 1 of the invention), and 25 g Borneol were mixed sufficiently with 40 g microcrystalline cellulose. 3% povidone-ethanol solution was added to soften the mixture. The mixture was then passed through 18# sieve, and dried at 60° C. for 30-45 minutes to give granules, 4 g talc was added and mixed thoroughly. The formed granules were compressed into tablets.

EXAMPLE 21

90 g of Radix salviae miltrorrhizae extract (CN Pat. Application CN1384090A, example 1), 150 g of Radix notoginseng extract (example 1 of the invention), 82 g of Radix astragali extract (example 1 of the invention), and 8 g Borneol were mixed sufficiently with 40 g microcrystalline cellulose. 3% povidone-ethanol solution solution was added to soften the mixture. The mixture was passed through 18# seive to form granulate and dried at 60° C. for 30-45 minutes. So obtained granules were trimed, and then 4 g talc was added and mixed thoroughly.

EXAMPLE 22

85 g of Radix Salviae Miltrorrhizae extract (CN Pat. Application CN1384090A, example 1), 135 g of Radix Notoginseng extract (example 1 of the invention), 80 g of the Radix Astragali extract (Teng Xing Long et al, *Hei Long Jiang Medical Journal,* 2002, 15(5): 340) and 30 g Borneol were mixed sufficiently with 700 g polyethylene glycol-6000, and fused. Then dropped into low temperature liquid paraffine, selected pills and removed low temperature liquid paraffine.

EXAMPLE 23

17 g of Radix Salviae Miltrorrhizae extract (CN Pat. Application CN1384090A, example 1), 280 g of Radix Notoginseng extract (example 1 of the invention), 17 g of Radix Astragali extract (example 1 of the invention, (Extraction: Yu Hao et al., *West China Journal of Pharmaceutical Sciences,* 1993, 8(3):163); Refinement: Teng Xing Long et al., *Hei Long Jiang Medical Journal,* 2002, 15(5): 340), and 16 g Borneol were mixed sufficiently with 700 g polyethylene glycol-6000, and fused. Then dropped into low temperature liquid paraffine, selected pills and removed low temperature liquid paraffine.

EXAMPLE 24

67 g of Radix Salviae Miltrorrhizae extract (CN Pat. Application CN1352985A, example 1), 180 g of Radix Notoginseng extract (example 1 of the invention), 67 g of Radix Astragali extract (example 1 of the invention), and 16 g oil of Lignum Dalbergiae Odoriferae were mixed sufficiently with 40 g microcrystalline cellulose. 3% povidone-ethanol solution was added to soften the mixture. The mixture was passed through 18# seive to form granules, and dried at 60° C. for 30-45 minutes. After trimed, 4 g talc was added and mixed thoroughly. The formed granules were filled into capsules.

EXAMPLE 25

60 g of Radix Salviae Miltrorrhizae extract (CN Pat. Application CN1384090A, example 1), 80 g of Radix Notoginseng extract (Tang Di Guang, *The journal of Chinese Traditional Patent Medicine,* 1990, 12(8): 5), 165 g of Radix Astragali extract (example 1 of the invention), and 25 g oil of Lignum Dalbergiae Odoriferae were mixed sufficiently with 40 g microcrystalline cellulose. 3% povidone-ethanol solution was added to soften the mixture. The mixture was passed through 18# seive to form granulate and dried at 60° C. for 30-45 minutes. After trimed, 4 g talc was added and mixed thoroughly. The formed granules were compressed into tablets.

EXAMPLE 26

90 g of Radix Salviae Miltrorrhizae extract (CN Pat. Application CN1384090A, example 1), 150 g of Radix Notoginseng extract (example 1 of the invention), 82 g of Radix Astragali extract (example 1 of the invention), and 8 g oil of Lignum Dalbergiae Odoriferae were mixed sufficiently with 40 g microcrystalline cellulose. 3% povidone-ethanol solution was added to soften the mixture. The mixture was passed through 18# seive to form granulate and dried at 60° C. for 30-45 minutes. After trimed, 4 g talc was added and mixed thoroughly. So obtained granules were trimed and packed.

EXAMPLE 27

85 g of Radix Salviae Miltrorrhizae extract (CN Pat. Application CN1384090A, example 1), 135 g of Radix Notoginseng extract (example 1 of the invention), 80 g of the Radix Astragali extract (Teng Xing Long et al, *Hei Long Jiang Medical Journal,* 2002, 15(5): 340) and 30 g oil of Lignum Dalbergiae Odoriferae were mixed sufficiently with 700 g polyethylene glycol-6000, and fused. Then dropped into low temperature liquid paraffine, selected pills and removed low temperature liquid paraffine.

EXAMPLE 28

17 g of Radix Salviae Miltrorrhizae extract (CN Pat. Application CN1384090A, example 1), 280 g of Radix Notoginseng extract (example 1 of the invention), 17 g of Radix Astragali extract (example 1 of the invention, Extraction: Yu Hao et al., *West China Journal of Pharmaceutical Sciences,* 1993, 8(3):163); Refinement: Teng Xing Long et al., Hei Long Jiang Medical Journal, 2002, 15(5): 340), and 16 g oil of Lignum Dalbergiae Odoriferae were mixed sufficiently with 700 g polyethylene glycol-6000, and fused. Then dropped into low temperature liquid paraffine, selected pills and removed low temperature liquid paraffine.

Experiment 1—Effects of the Present Pharmaceutical Compositions on Localized Cerebral Ischemia in Rats
1. Materials
  a. Animals: Male Sprague-Dawley (SD) rats, weighing 180-200 gram, Quality Control Certificate number SCXK (Beijing) 2002-0003, provided by Beijing Weitong Lihua Experimental Animal Technology Co., Limited.
  b. Tested drugs and Chemical Agents:
  Tested drugs: the composition obtained in the present example 1 and example 2; the extract of Radix Salviae Miltiorrhizae in the present example 1; the extract of Radix notoginseng in the present example 1; the extract of Radix Astragali in the present example 1; oil of Lignum Dalbergiae Odoriferae and Borneol. XUESAI-TONG (Trade Name) was purchased from the market, made by Qunming Pharmaceutical Co., Limited, lot number 20020922.03.
  Chemical Agent: 2,3,5-Triphenyltetrazolium chloride (TTC), light yellowish powder, product of Beijing Mashi Fine Chemical Co., Limited, lot number 011102.
  c. Experimental Instruments: XTT stereoscopic microscope, product of Yunnan Optical Instrument Factory; Model AEG-220 Electronic Analytical Scale, product of Japan Shimadzu Corporation; 307-6 Desktop Dental Instrument Cart, product of Shanghai Dental Medical Instrument Factory; HZQ-C Air Bath Vibrator, product of Harbin Dongming Medical Instrument Factory.
2. Methods and Results
  a. Group and the administration of investigational products: The animals were randomly grouped per weight. The animals in all groups were administrated the tested investigational products via sublingual vein 30 minutes after the operation. The tested investigational products were also given via intraperitoneal injection at 2 hours and 23 hours after the operation. All products were diluted with physiological saline to desired concentration. Amount of injection was 0.4 ml per 100 g body weight.
  b. The model of middle cerebral artery embolism: Rats were anaesthetized by given 10% chloral hydrate solution (350 mg/kg) via intraperitoneal and were fixed on right lateral position. A 1.5 cm length curve incision was made from the middle point between outer corner of left eye and left external auditory canal. Cut off and excise the temporalis muscle, expose the temporal bone, and under stereoscopic microscope, open a 2.5 mm diameter bone window at the position which is on the joint of zygomatic bone and squamosal temporal bone and is only 1 mm from the mouth end of the joint. Cleared the debris and exposed the middle cerebral artery (which was located between olfactory bundle and inferior cerebral vein); Placed a small piece of plastic film to protect the area surrounding the blood vessel. Placed a small piece of quantitative filter paper soaked with 10 µl 50% iron chloride(III) over this segment of the middle cerebral artery, 30 minutes later, took the filter paper off and washed the topical tissues with physiological saline, sutured the incision in layers. The rats were returned to cage and recovered in normal living condition. The room temperature was controlled at 24° C.
  c. Score Criteria of Neurological Symptoms
  Behavior assessments were conducted at 24 hours after the operation. Score criteria were as follows: (1). Observed the flex condition of forelimbs after lifting the rats by their tails; it would be recorded as 0 point if both forelimbs extended forward symmetrically; 1 point if there are shoulder flexion, elbow flexion, and/or shoulder intorsion on the forelimb at opposite side of the operation. (2). Placed the rat on the flat surface, pushed both of the shoulder towards the opposite sides and checked the resistance. It would be recorded as 0 point if the resistance is equal and strong in both sides; 1 point if the resistance in the opposite side of the operation decreased. (3). Placed the forelimbs of the rat on a metal mesh and observe the muscle tension. It would be recorded as 0 point if the muscle tension in both sides were equal and strong; 1 point if the muscle tension of the forelimb at opposite side of the operation decreased. (4). It would record as 1 point if the rat continuously rotates towards the opposite side of the operation after it was lifted by its tail.
  Based on the above scoring criteria, full score is 4 points. The higher the score is, the more severe the behavior disability is.
  d. The Determination of the Extent of Cerebral Infarction
  The rats were decapitated after the behavior assessments were completed. The brains were collected. Discarded olfactory bulb, cerebellum and lower brain stem, the rest of the brain was sagittally excised into 5 slices. Immersed the 5 slices of the brain into TTC dye solution (every 5 ml dye solution contain 4% TTC 1.5 ml, 1 M $K_2HPO_4$ 0.1 ml, then added distilled water to the mark), incubated at 37° C. in dark for 30 minutes, moved the brain slices to 10% Formaldehyde solution and stored 24 hours in dark. By dyeing, non-ischemic area was in rose-red, but ischemic area was in white. White tissues from the brain slices were carefully cut out and weighed. The weight percentage of the infarction tissues in the whole brain and in the damage side of the brain were regarded as the extent of brain infarction.

e. Results:

TABLE 1

The Effects of the Present Pharmaceutical Compositions and Extracts on Neurological Symptoms in Rats (MCAO) ($\bar{x} \pm s$)

| Groups | Dosage (mg/kg body weight) | Number of Animals | Score of Neurological symptoms after 6 Hours | Score of Neurological symptoms after 24 Hours |
|---|---|---|---|---|
| Pharmaceutical Composition in the present example 1 (Radix Salviae Miltiorrhizae Extract + Radix Notoginseng Extract + Radix Astragali Extract + Borneol) | 5 + 10 + 5 + 2 | 10 | 1.22 ± 0.41**##&&@ | 1.07 ± 0.59**##&&@ |
| Pharmaceutical Composition in Example 2 (Radix Salviae Miltiorrhizae Extract + Radix Notoginseng Extract + Radix Astragali Extract + Oil of Lignum Dalbergiae Odoriferae) | 5 + 10 + 5 + 2 | 10 | 1.32 ± 0.45**##&&@ | 1.13 ± 0.56**##&&@ |
| Salvinolic Acids + Radix Notoginseng Saponins + Borneol | 6 + 12 + 2 | 10 | 1.68 ± 0.43**##& | 1.61 ± 0.63**##& |
| Salvinolic Acids + Radix Notoginseng Saponins | 6.7 + 13.3 | 10 | 2.14 ± 0.60**# | 2.14 ± 0.59**# |
| Salvinolic Acids | 20 | 10 | 2.95 ± 0.67* | 2.57 ± 0.42* |
| Radix Notoginseng Saponins | 20 | 10 | 2.65 ± 0.32* | 2.52 ± 0.51* |
| XUESAITONG | 20 | 10 | 2.65 ± 0.37* | 2.56 ± 0.54* |
| Control Group | | 10 | 3.22 ± 0.42 | 3.04 ± 0.53 |

Note:
*$P < 0.05$,
**$P < 0.01$, in compare with control group;
$P < 0.05$,
$P < 0.01$, in compare with Salvinolic Acids group or Radix Notoginseng Saponins group;
&$P < 0.05$,
&&$P < 0.01$, in compare with Salvinolic Acids + Radix Notoginseng Saponins group;
@$P < 0.05$ in compare with Salvinolic Acids + Radix Notoginseng Saponins + Borneol group.
MCAO—Middle Cerebral Artery Occlusion

TABLE 2

The Effects of the Present Pharmaceutical Compositions and Extracts on the Area of Cerebral Infarction in Rats (MCAO) ($\bar{x} \pm s$)

| Groups | Dosage (mg/kg body weight) | Number of Animals | Cerebral Infarction/whole brain (%) | Cerebral Infarction/Damaged side of brain (%) |
|---|---|---|---|---|
| Pharmaceutical Composition in the present example 1 (Radix Salviae Miltiorrhizae Extract + Radix Notoginseng Extract + Radix Astragali Extract + Borneol) | 5 + 10 + 5 + 2 | 10 | 1.28 ± 0.74**##&&@ | 2.57 ± 1.41**##&&@ |
| Pharmaceutical Composition in Example 2 (Radix Salviae Miltiorrhizae Extract + Radix Notoginseng Extract + Radix Astragali Extract + Oil of Lignum Dalbergiae Odoriferae) | 5 + 10 + 5 + 2 | 10 | 1.34 ± 0.69**##&&@ | 2.61 ± 1.50**##&&@ |
| Salvinolic Acids + Radix Notoginseng Saponins + Borneol | 6 + 12 + 2 | 10 | 1.66 ± 0.69**##& | 3.37 ± 1.30**##& |
| Salvinolic Acids + Radix Notoginseng Saponins | 6.7 + 13.3 | 10 | 2.32 ± 0.84**# | 4.61 ± 1.80**# |
| Salvinolic Acids | 20 | 10 | 3.21 ± 0.86* | 6.41 ± 1.76* |
| Radix Notoginseng Saponins | 20 | 10 | 3.02 ± 1.21* | 5.99 ± 2.33* |
| XUESAITONG | 20 | 10 | 2.99 ± 1.11* | 5.98 ± 2.23* |
| Control Group | | 10 | 4.33 ± 0.81 | 8.69 ± 1.59 |

Note:
*$P < 0.05$,
**$P < 0.01$, in compare with control group;
$P < 0.05$,
$P < 0.01$, in compare with Salvinolic Acids group or Radix Notoginseng Saponins group;
&$P < 0.05$,
&&$P < 0.01$, in compare with Salvinolic Acids + Radix Notoginseng Saponins group;
@$P < 0.05$ in compare with Salvinolic Acids + Radix Notoginseng Saponins + Borneol group.

The results in Table 1 and 2 show that all tested drugs have significant effects of anti-cerebral ischemia. Of all drugs, the composition in the present example 1 (Radix Salviae Miltiorrhizae extract, Radix Notoginseng extract, Radix Astragali extract and Broneol) and the composition in the present example 2 (Radix salviae miltiorrhizae extract, Radix notoginseng extract, Radix Astragali extract and oil of Lignum Dalbergiae Odoriferae) achieve the significant therapeutic effects. Only administering salvinolic acids or radix notoginseng saponins has the similar effects with administering XUESAITONG (Trade Name, positive control drug); The therapeutic effects of administering the combination of salvinolic acids plus radix notoginseng saponins plus broneol is better than that of administering salvinolic acids plus radix notoginseng saponins or salvinolic acids only or radix notoginseng saponins only or XUESAITONG (Trade Name,), but it is worse than that of the pharmaceutical composition in the present example 1 and the pharmaceutical composition in the present example 2.

By using the model of experimental cardiac infarction in rats and extracorporeal perfusion method, the present invention compares the effects of anti-myocadial ischemia of the pharmaceutical composition of present invention, salvinolic acids plus radix notoginseng saponins plus Broneol or oil of Lignum Dalbergiae Odoriferae, salvinolic acids plus radix notoginseng saponins, salvianolic acids and radix notoginseng saponins. The results show that the pharmaceutical composition of present invention has significant anti-myocardial ischemia effects. Its therapeutic effects are better than that of applying only salvinolic acids orradix notoginseng saponins, stronger than that of administering salvinolic acids plus radix notoginseng saponins, and better than that of salvianolic acids plusradix notoginseng saponins plus Broneol or oil of Lignum Dalbergiae Odoriferae. The results indicate that the pharmaceutical composition of present invention , i.e., Radix Salviae Miltiorrhizae extract plus Radix Notoginseng extract plus Radix Astragali extract and Broneol, or Radix Salviae Miltiorrhizae extract plus Radix Notoginseng extract plus Radix Astragali extract and oil of Lignum Dalbergiae doriferae, the four of them have strong synergic actions.

Experiment 2 The Studies on the Anti-Myocardial Ischemia Effects of the Present Compositions 1. Group and the administering of investigational products:
   70 male Wistar rats, weight 250.8±24.6 gram, were randomly divided into seven drug groups per their weight: physiological saline as control, XUESAITONG, salvinolic acids, radix notoginseng saponins, salvinolic acids plusradix notoginseng saponins, the pharmaceutical compositions in the present example 1 and the pharmaceutical compositions in the present example 2. All tested drugs are diluted with physiological saline to the desired concentrations; the tested drugs were administered at 4 ml/kg via tail vein injection.

2. Method
   a. Model of the experimental myocardial infarction on rats: The rats were anaesthetized with pentobarbital sodium (45 mg/kg) via intraperitoneal injection, fixed in supine position, and were inserted with a trachea tube, a 2 cm longitudinal incision was made along the left side of sternum. After opening the thoracic cavity, cut off the third and fourth rib on its cartilage section closed to the sternum, maintained respiration on a artificial respiration apparatus (ventilation volume 2 ml/100 g, 50 times/minute.). Opened the pericardial membrane and exposed the heart, put the string underneath the left descending coronary artery of heart for ligation, record the standard II lead electrocardiogram. Stabilized for 10 minutes, then ligated the left descending coronary artery of heart and close the thoracic cavity. Sucked out the secreted substances in larynx with a syringe and made the rats return to self respiration. 15 minutes after the ligation of coronary artery, the tested drugs are given via vein. Obtained the heart 4 hours after the ligation of coronary artery, and excised the section of the heart below the ligation string and cut into 5 slices, dyed the heart slices with nitroblue tetrazolium (NBT). Calculated the area percentage of myocardial infarction over the area of the ventricles as well as the whole heart, and analyzed with statistical method (t-test).
   b. Isolated Perfused (Langendorff) Heart Experiment: Refered "Experimental Methodology of Pharmacology" (edited by Shuyun Xu etc., People Health Press, third edition, January 2002)

3. Results
   a. The Effect on the area of myocardial infarction in rats, see Table 3.

TABLE 3

The Effects of the Present Pharmaceutical Compositions and Extracts on the Area of Myocardial Infarction in Rats (MCAO) ($\bar{x} \pm s$)

| Groups | Dosage (mg/kg body weight) | Number of Animals | Infarction Area/ Ventricle Area (%) | Infarction Area/ Whole Heart (%) |
|---|---|---|---|---|
| Pharmaceutical Composition in the present example 1 (*Radix Salviae Miltiorrhizae* Extract + *Radix Notoginseng* Extract + *Radix Astragali* Extract + Borneol) | 5 + 10 + 5 + 2 | 10 | 12.53 ± 4.57**\*##&@ | 10.96 ± 3.35**\*##&@ |
| Pharmaceutical Composition in the present example 2 (*Radix Salviae Miltiorrhizae* Extract + *Radix Notoginseng* Extract + *Radix Astragali* Extract + Oil of *Lignum Dalbergiae Odoriferae*) | 5 + 10 + 5 + 2 | 10 | 12.62 ± 4.49**\*##&@ | 11.01 ± 3.42**\*##&@ |
| Salvinolic Acids + *Radix Notoginseng* Saponins + Borneol | 6 + 12 + 2 | 10 | 16.72 ± 6.43**\*##& | 13.15 ± 4.16**\*##& |
| Salvinolic Acids + *Radix Notoginseng* Saponins | 6.7 + 13.3 | 10 | 20.51 ± 6.58**\# | 14.03 ± 5.18**\# |

TABLE 3-continued

The Effects of the Present Pharmaceutical Compositions and Extracts
on the Area of Myocardial Infarction in Rats (MCAO) ($\bar{x} \pm s$)

| Groups | Dosage (mg/kg body weight) | Number of Animals | Infarction Area/ Ventricle Area (%) | Infarction Area/ Whole Heart (%) |
| --- | --- | --- | --- | --- |
| Salvinolic Acids | 20 | 10 | 24.08 ± 8.56* | 18.11 ± 4.49* |
| Radix Notoginseng Saponins | 20 | 10 | 25.97 ± 4.65* | 21.03 ± 3.82* |
| XUESAITONG | 20 | 10 | 25.02 ± 5.72* | 19.64 ± 4.71* |
| Control Group | | 10 | 33.67 ± 7.85 | 26.48 ± 5.11 |

Note:
*$P < 0.05$,
**$P < 0.01$, in compare with control group;
$P < 0.05$,
$P < 0.01$, in compare with Salvinolic Acids group or Radix Notoginseng Saponins group;
&$P < 0.05$,
&&$P < 0.01$, in compare with Salvinolic Acids + Radix Notoginseng Saponins group;
@$P < 0.05$ in compare with Salvinolic Acids + Radix Notoginseng Saponins + Borneol group.

b. Effect on flow volume in coronary artery and heart rate on isolated heart of guinea pig, see Table 4.

TABLE 4

The Effects of the Present Pharmaceutical Compositions and Extracts
on the Flow Volume in Coronary Artery and Heart Rate On Isolated heart of
Guinea Pig ($\bar{x} \pm s$)

| Groups | Dosage (mg/kg body weight) | Number of Animals | Increasing Value of Flow Volume of Coronary Artery (ml/min) | Decreasing Value of Heart Rate (beat/min) |
| --- | --- | --- | --- | --- |
| Pharmaceutical Composition in the present example 1 (Radix Salviae Miltiorrhizae Extract + Radix Notoginseng Extract + Radix Astragali Extract + Borneol) | 5 + 10 + 5 + 2 | 10 | 16.67 ± 1.74**&&# | 40 ± 14**&&# |
| Pharmaceutical Composition in the present example 2 (Radix Salviae Miltiorrhizae Extract + Radix Notoginseng Extract + Radix Astragali Extract + Oil of Lignum Dalbergiae Odoriferae) | 5 + 10 + 5 + 2 | 10 | 16.76 ± 1.68**&&# | 41 ± 15**&&# |
| Salvinolic Acids + Radix Notoginseng Saponins + Borneol | 6 + 12 + 2 | 10 | 14.85 ± 1.76**& | 32 ± 12**& |
| Salvinolic Acids + Radix Notoginseng Saponins | 6.7 + 13.3 | 10 | 11.34 ± 2.24* | 21 ± 9* |
| Salvinolic Acids | 20 | 10 | 7.91 ± 1.36 | 9 ± 4 |
| Radix Notoginseng Saponins | 20 | 10 | 8.88 ± 1.51 | 10 ± 5 |
| XUESAITONG | 20 | 10 | 8.82 ± 1.11 | 10 ± 4 |

Note:
*$P < 0.05$,
**$P < 0.01$, in compare with control group; Salvinolic Acids group or Radix Notoginseng Saponins group or XUESAITONG;
&$P < 0.05$,
&&$P < 0.01$, in compare with Salvinolic Acids + Radix Notoginseng Saponins group;
$P < 0.05$, in compare with Salvinolic Acids + Radix Notoginseng Saponins + Borneol group.

The results from table 3 and 4 show that all tested drugs have significant effects of anti-myocardial ischemia. Of all drugs, the composition in the present present example 1 (Radix Salviae Miltiorrhizae extract, Radix Notoginseng extract, Radix Astragali extract and Broneol) and the pharmaceutical composition in present example 2 (Radix Salviae Miltiorrhizae extract, Radix Notoginseng extract, Radix Astragali extract and oil of Lignum Dalbergiae Odoriferae) have shown the best therapeutic effects. Only administering salvinolic acids or radix notoginseng saponins has the similar effects with administering XUESAITONG (positive control drug); The therapeutic effects of administering the combination of salvinolic acids plus radix notoginseng saponins plus Broneol is better than that of administering salvinolic acids plus radix notoginseng saponins or salvinolic acids only or radix notoginseng saponins only or XUESAITONG only, but it is worse than that of the pharmaceutical composition in the present example 1 and the pharmaceutical composition in the present example 2.

We claim:

1. A Pharmaceutical composition comprising:
   5.0%-70.0% by weight Radix Salviae Miltiorrhizae extract;
   10.0%-85.0% by weight Radix Notoginseng extract;
   5.0%-70.0% by weight Radix Astragali extract; and 1.0%-15.0% by weight Borneol or oil of Lignum Dalbergiae Odoriferae, wherein said Radix Salviae Miltiorrhizae extract comprises 45% -70% by weight salvianolic acid B, 2% -10% by weight salvianolic acid E, 4% -20% by weight rosmarinic acid, 1%-10% by weight lithospermic acid, and more than 70% by weight salvinolic acids;

said Radix Notoginseng extract comprises 2% -10% by weight notoginsenoside R1, 2% -6% by weight ginsenoside Re, 15% -40% by weight ginsenoside Rg1, 15%-40% by weight ginsenoside Rb1, 5% -12% by weight ginsenoside Rd, and more than 70% by weight radix notoginseng saponins; and said Radix Astragali extract comprises 5% -15% by weight astragaloside I and more than 70% by weight Radix Astragali saponins.

2. The composition of claim 1, comprising
15.0%-50.0% by weight Radix Salviae Miltiorrhizae extract;
25.0%-65.0% by weight Radix Notoginseng extract;
15.0%-50.0% by weight Radix Astragali extract; and
2.0%-12.0% by weight Borneol or oil of Lignum Dalbergiae Odoriferae.

3. The composition of claim 2, comprising
20.0%-30.0% by weight Radix Salviae Miltiorrhizae extract;
30.0%-55.0% by weight Radix Notoginseng extract;
20.0%-30.0% by weight Radix Astragali extract; and
4.0%-10.0% by weight Borneol or oil of Lignum Dalbergiae Odoriferae.

4. The composition of claim 3, comprising
23% by weight Radix Salviae Miltiorrhizae extract;
45.0% by weight Radix Notoginseng extract;
23% by weight Radix Astragali extract; and
9% by weight Borneol or oil of Lignum Dalbergiae Odoriferae.

5. The composition of claims 1, wherein said Radix Salviae Miltiorrhizae extract comprises more than 80% by weight salvinolic acids; said Radix Notoginseng extract comprises more than 80% by weight radix notoginseng saponins; and said radix astragali extract comprises more than 80% by weight radix astragali saponins.

6. The composition of claims 1, wherein the composition is in the dosage form of an injection, tablets, sustained-release tablets, drop pills, granules, injection powder, capsules, or microgranules.

7. The composition of claim 6, wherein the composition is injection or injection powder.

8. A method for treating cardiovascular and cerebrovascular diseases in a subject, comprising administrating the composition of claim 1 to said subject in need of such treatment.

9. A method for treating cardiovascular and cerebrovascular diseases in a subject, comprising administrating the composition of claim 2 to said subject in need of such treatment.

10. A method for treating cardiovascular and cerebrovascular diseases in a subject, comprising administrating the composition of claim 3 to said subject in need of such treatment.

11. A method for treating cardiovascular and cerebrovascular diseases in a subject, comprising administrating the composition of claim 4 to said subject in need of such treatment.

12. A method for treating cardiovascular and cerebrovascular diseases in a subject, comprising administrating the composition of claim 5 to said subject in need of such treatment.

13. A method for treating cardiovascular and cerebrovascular diseases in a subject, comprising administrating the composition of claim 6 to said subject in need of such treatment.

14. A method for treating cardiovascular and cerebrovascular diseases in a subject, comprising administrating the composition of claim 7 to said subject in need of such treatment.

* * * * *